US00PP28746P3

(12) United States Plant Patent
van Duijnhoven

(10) Patent No.: US PP28,746 P3
(45) Date of Patent: Dec. 5, 2017

(54) *ASPLENIUM* PLANT NAMED 'VITASPHUR'

(50) Latin Name: *Asplenium antiquum*
Varietal Denomination: VITASPHUR

(71) Applicant: Vitro Plus, B.V., Burgh-Haamstede (NL)

(72) Inventor: Henk van Duijnhoven, Mariahout (NL)

(73) Assignee: Vitro Plus, B.V., Burgh-Haamstede (NL)

( * ) Notice: Subject to any disclaimer, the term of this patent is extended or adjusted under 35 U.S.C. 154(b) by 91 days.

(21) Appl. No.: 14/998,588

(22) Filed: Jan. 22, 2016

(65) Prior Publication Data

US 2017/0215315 P1 Jul. 27, 2017

(51) Int. Cl.
*A01H 5/00* (2006.01)

(52) U.S. Cl.
USPC ..... Plt./379

(58) Field of Classification Search
USPC ..... Plt./373, 379
See application file for complete search history.

(56) References Cited

U.S. PATENT DOCUMENTS

PP8,061 P * 12/1992 Beck ..... A01H 9/00
Plt./88.3

* cited by examiner

*Primary Examiner* — Susan McCormick Ewoldt
*Assistant Examiner* — Karen Redden
(74) *Attorney, Agent, or Firm* — Samuel R. McCoy, Jr.

(57) ABSTRACT

A new and distinct *Asplenium antiquum* cultivar named 'VITASPHUR' which is characterized by strongly carinate leaves, moderately undulate leaf margins, a unique growth habit with leaves that twist and curl in a clockwise orientation, and the stability of these characteristics from generation to generation.

4 Drawing Sheets

Latin name of the genus and species: The Latin name of the genus and species of the novel variety disclosed herein is *Asplenium antiquum.*

Variety denomination: The inventive variety of *Asplenium antiquum* disclosed herein has been given the variety denomination 'VITASPHUR'.

BACKGROUND OF THE INVENTION

Parentage: 'VITASPHUR' is the product of a breeding program conducted at the inventor's nursery in Mariahout, the Netherlands. In early 2012, spores were harvested from a nursery collection of an unnamed *Asplenium antiquum* plants, and subsequently sown at the applicant's nursery in Mariahout, the Netherlands. The resulting sporophytes were then grown to a mature size for evaluation. Some of these plants, those that exhibited unique characteristics, were then cloned by way of meristematic tissue culture. The resulting mericlones were then grown to a mature size for evaluation, to determine potential commercial value. 'VITASPHUR' was ultimately selected for commercialization in October of 2013 due to its unique curled and twisted foliage.

Asexual Reproduction: Asexual reproduction of the new cultivar 'VITASPHUR', by way of mericloning, was first initiated in February of 2014 at a commercial laboratory in Burgh-Haamstede, The Netherlands. Through subsequent generations, the unique features of this cultivar have proven to be stable and true to type.

SUMMARY OF THE INVENTION

The cultivar 'VITASPHUR' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'VITASPHUR'. These characteristics in combination distinguish 'VITASPHUR' as a new and distinct *Asplenium antiquum* cultivar:

1. *Asplenium antiquum* 'VITASPHUR' exhibits strongly carinate leaves; and
2. *Asplenium antiquum* 'VITASPHUR' exhibits moderately undulate leaf margins; and
3. *Asplenium antiquum* 'VITASPHUR' exhibits a unique growth habit with leaves that twist and curl in a clockwise orientation.

BOTANICAL DESCRIPTION OF THE PLANT

Figure 1:
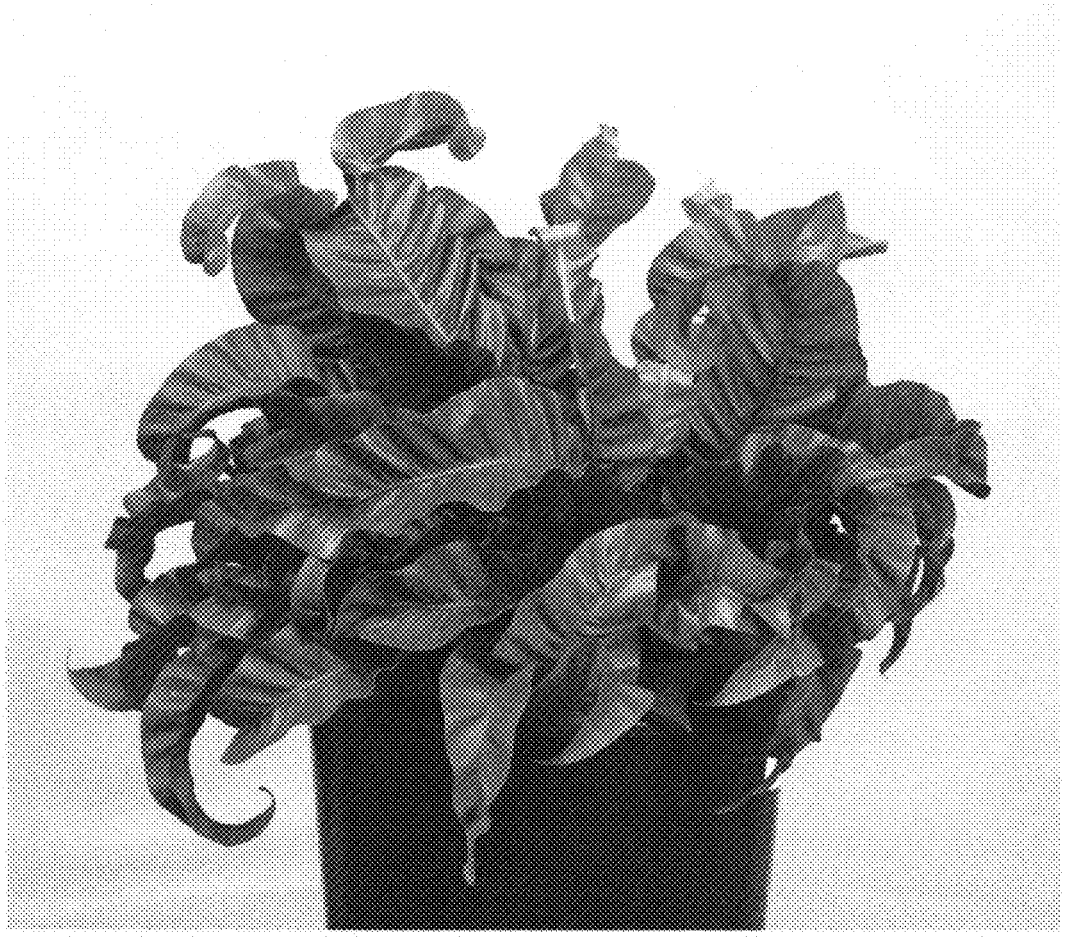
FIG. 1 illustrates, as nearly true as it is reasonably possible to make the same in color photographs of this type, an exemplary plant of 'VITASPHUR' grown in a commercial greenhouse in Mariahout, the Netherlands. This plant is approximately 2 years old, shown planted in a 12 cm container.
Figure 2:
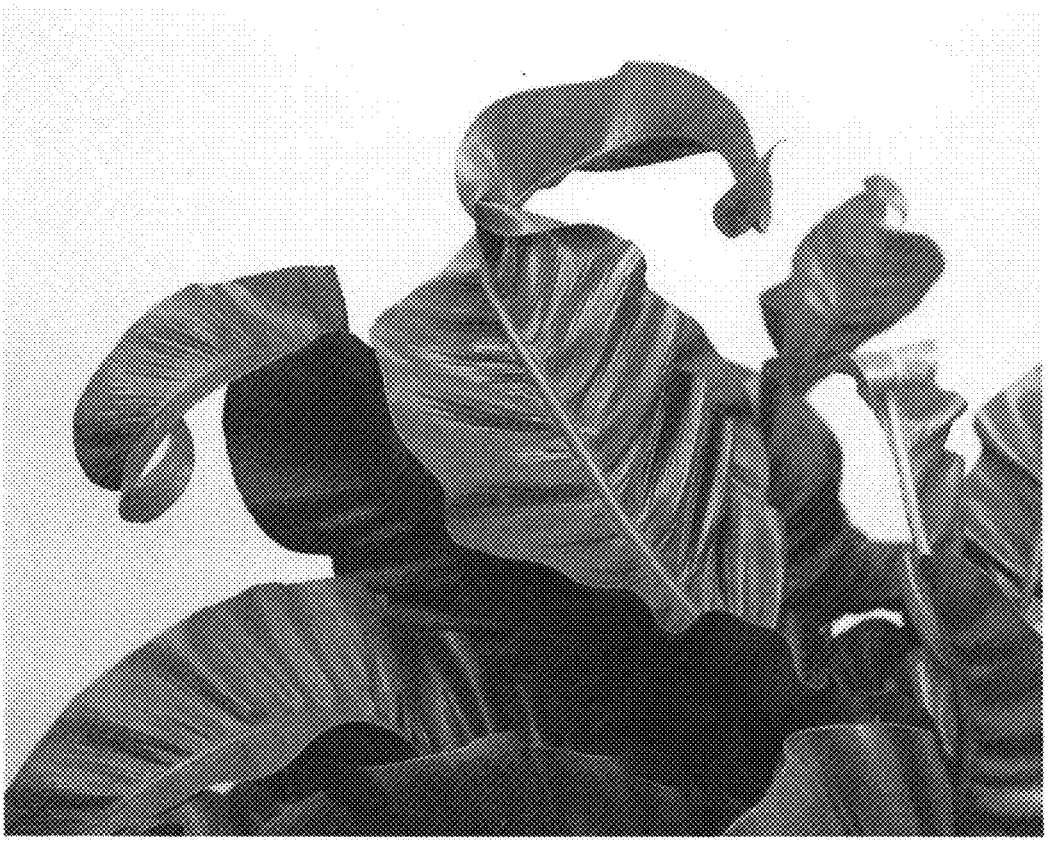
FIG. 2 illustrates, as nearly true as it is reasonably possible to make the same in color photographs of this type, the typical apical foliage habit of 'VITASPHUR'.
Figure 3:
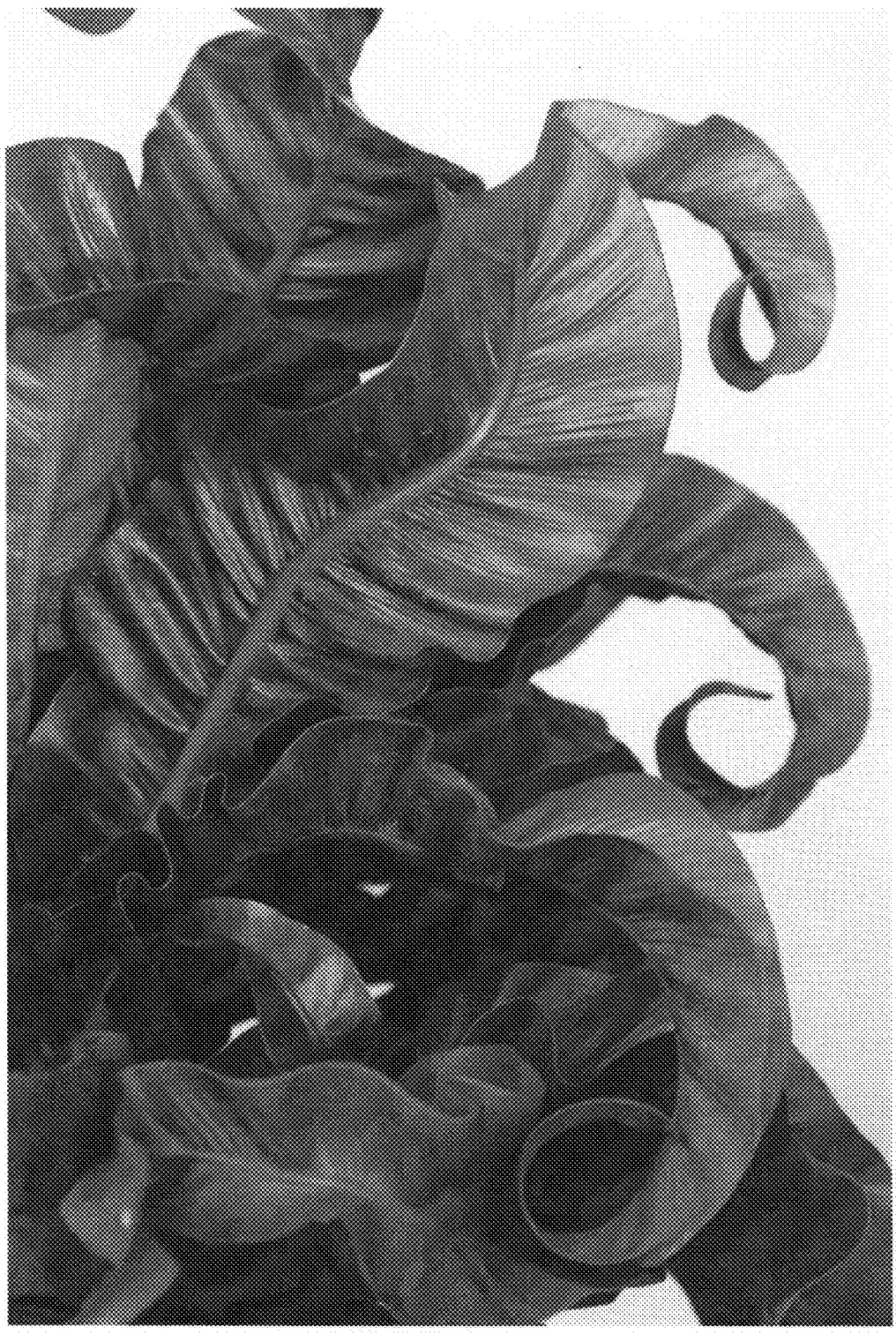
FIG. 3 illustrates, as nearly true as it is reasonably possible to make the same in color photographs of this type, the typical axial foliage habit of 'VITASPHUR'.
Figure 4:
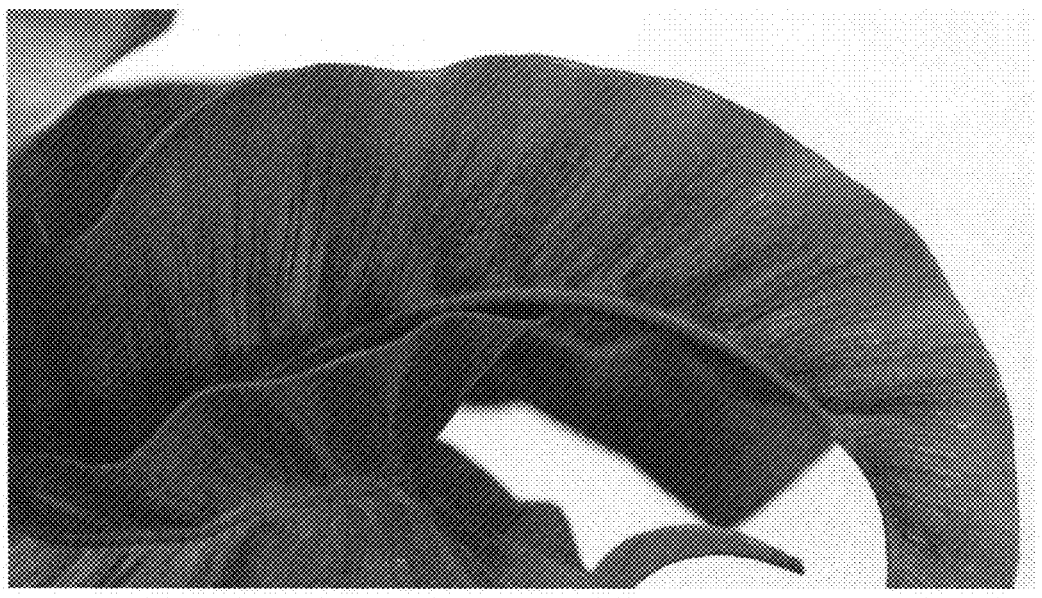
FIG. 4 illustrates, as nearly true as it is reasonably possible to make the same in color photographs of this type, the sori of 'VITASPHUR'.

The following observations and measurements made in December of 2015 describe averages from a sample set of six specimens of 2 year-old 'VITASPHUR' plants grown in 12 cm nursery containers at a greenhouse in Mariahout, the Netherlands. Plants were produced using conventional greenhouse production protocols which consisted of overhead irrigation, liquid fertilizer applications, and chemical pest control measures as required. Temperatures ranged from approximately 5 to 15 degrees Celsius during the day and 1 to 12 degrees Celsius at night. No photoperiodic treatments or artificial light was given to the plants.

Those skilled in the art will appreciate that certain characteristics will vary with older or, conversely, with younger plants. 'VITASPHUR' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climatic and cultural conditions. Color notations are based on *The Royal Horticultural Society Colour Chart*, The Royal Horticultural Society, London, 2015 (sixth edition).

A botanical description of 'VITASPHUR' and a comparison with the parent and closest known comparator, *Asplenium antiquum*, is provided below.

Plant description:

*Growth habit*.—Herbaceous perennial; leaves growing from a basal rosette forming a globular-shaped plant.

*Height from soil level to top of foliar plane*.—47.8 cm, on average.

*Plant spread*.—Average of 64.0 cm.

*Growth rate*.—Moderate.

*Plant vigor*.—Moderate.

*Propagation*.—Type 13 Mericloning. Time to initiate roots — Approximately 80 days at about 25 degrees Celsius. Time to produce a rooted cutting — Approximately 105 days at 20 to 25 degrees Celsius. No pinching is required. Crop time — Approximately 26 weeks from propagation to marketable plant.

*Disease and pest resistance or susceptibility*.—Similar to other *Asplenium antiquum* varieties.

*Environmental tolerances*.—Adapt to, at least, USDA Zones 10B to 13 and temperatures as high as 35 degrees Celsius; high tolerance to rain; moderate tolerance to wind.

Root system:

*General*.—Fine, well-branched fibrous roots which are brown in color, nearest to RHS 200C.

Foliage:

*Arrangement*.—Alternate; growing in basal rosettes.

*Quantity*.—Approximately 62 leaves per plant.

*Dimensions*.—36.2 cm long and 9.0 cm wide, on average.

*Shape*.—Lanceolate.

*Aspect*.—Moderately to strongly carinate; moderately twisted and curled.

*Apex*.—Acuminate; strongly curled to near cirrhose.

*Base*.—Obtuse.

*Margin*.—Entire; moderately undulate.

*Pubescence, texture and luster of adaxial surface*.—Glabrous, smooth, and glossy; proximal portion on the main vein is moderately covered with a thin papery layer, colored greyed-brown between RHS 199B and N199B.

*Pubescence, texture and luster of abaxial surface*.—Glabrous, smooth, and moderately glossy; proximal portion on the main vein is moderately covered with a thin papery layer, colored greyed-brown between RHS 199B and N199B.

*Color*.—Juvenile foliage, adaxial surface — Yellow-green, near RHS 144A. Juvenile foliage, abaxial surface — Yellow-green, near RHS 144A. Mature foliage, adaxial surface — Green, in between near RHS 137B and 143A; general tonality is closest to 137B. Mature foliage, abaxial surface — Green, near RHS 137C, and yellow-green, near RHS 146B; general tonality is closest to 137B.

*Venation*.—Pinnate with free simple veins.

*Venation color, adaxial surface*.—The main vein is green, near RHS 143A, to yellow-green, near 144A; base is brown near RHS 200A and 200B, and darker. Secondary veins are green, in between near 137B and 143A yet closest to 137B.

*Venation color, abaxial surface*.—The main vein is yellow-green, near 144A; the proximal one-third to one-half is brown near RHS 200A and 200B, and darker. Secondary veins are is green, near RHS 137C, to yellow-green, near 146B yet closest to 137B.

*Petiole*.—No petioles present, leaves sessile.

Sori:

*Arrangement*.—Linear.

*Length*.—Approximately 2.6 cm.

*Diameter*.—Approximately 0.5 cm.

*Quantity of sori per leaf*.—300, on average.

*Quantity of sori per plant*.—Over 15,000.

*Sori color*.—Brown, near RHS 200A.

*Spore color*.—Greyed-orange, near RHS 163B.

COMPARISONS WITH THE PARENT PLANT

Plants of the new cultivar 'VITASPHUR' differ from the parent, an unnamed *Asplenium antiquum* plant, in the following characteristics:

1. 'VITASPHUR' exhibits foliage which is moderately carinate, moderately twisted and moderately curled, whereas the foliage of *Asplenium antiquum* is only slightly carinate and slightly arched downward.
2. 'VITASPHUR' exhibits moderately undulate leaf margins, whereas the leaf margins of *Asplenium antiquum* are only slightly undulate.
3. 'VITASPHUR' exhibits a unique growth habit with leaves that twist and curl in a clockwise orientation, whereas *Asplenium antiquum* exhibits an upright growth habit.

COMPARISONS WITH THE MOST SIMILAR COMMERCIAL VARIETY

Plants of the new cultivar 'VITASPHUR' differ from the closest known commercial comparator, *Asplenium antiquum* 'Victoria' (U.S. Plant Pat. No. 8,061), in the following characteristics:

1. 'VITASPHUR' exhibits foliage which is thicker than that of 'Victoria'.
2. 'VITASPHUR' exhibits foliage which is darker green than that of 'Victoria'.

3. 'VITASPHUR' exhibits moderately undulated leaf margins, whereas the leaf margins of 'Victoria' are heavily undulated.
4. 'VITASPHUR' exhibits leaves that twist in a clockwise orientation, whereas the leaves of 'Victoria' are not twisted.
5. The leaves of 'VITASPHUR' are more heavily reflexed than the leaves of 'Victoria'.

That which is claimed is:

1. A new and distinct variety of *Asplenium antiquum* plant named 'VITASPHUR', substantially as described and illustrated herein.

* * * * *